(12) United States Patent
Grotta et al.

(10) Patent No.: US 6,503,916 B2
(45) Date of Patent: Jan. 7, 2003

(54) TREATMENT OF ISCHEMIC BRAIN INJURY

(75) Inventors: James C Grotta, Bellaire, TX (US); Roger A Strong, Humble, TX (US); Jaroslaw Adam Aronowski, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/150,898

(22) Filed: May 17, 2002

(65) Prior Publication Data

US 2002/0169179 A1 Nov. 14, 2002

Related U.S. Application Data

(63) Continuation-in-part of application No. 09/552,924, filed on Apr. 20, 2000.
(60) Provisional application No. 60/131,116, filed on Apr. 27, 1999.

(51) Int. Cl.$^7$ ............................................. A61K 31/522
(52) U.S. Cl. ........................ 514/263.31; 607/96; 514/2; 514/161; 514/165
(58) Field of Search ....................... 514/263.31; 607/96

(56) References Cited

U.S. PATENT DOCUMENTS 5,248,678 A * 9/1993 Costa et al. ................. 514/220

* cited by examiner

*Primary Examiner*—Frederick Krass
(74) *Attorney, Agent, or Firm*—Gardere Wynne Sewell LLP; Sanford E. Warren, Jr.; Thomas C. Wright

(57) ABSTRACT

A composition and method adapted for the treatment of ischemic brain injury is disclosed, which includes applying hypothermic conditions to a subject within 5 hours after onset of brain injury and administering to the subject in need thereof a dose of a pharmaceutically effective amount of caffeine and at least a pharmaceutically effective amount of an alcohol or mixtures thereof adapted for the treatment of cerebral ischemia under hypothermic conditions.

21 Claims, 2 Drawing Sheets

TREATMENT OF ISCHEMIC BRAIN INJURY

This is a Continuation-In-Part of U.S. Ser. No. 09/552,924 filed Apr. 20, 2000, which claims priority to United States Provisional Patent Application Serial No. 60/131,116, filed Apr. 27, 1999.

TECHNICAL FIELD OF THE INVENTION

The present invention relates in general to the field of ischemic brain injury; and more particularly, to neuroprotective method and composition adapted for the treatment of cerebral ischemia.

BACKGROUND OF THE INVENTION

Without limiting the scope of the invention, its background is described in connection with the treatment of Ischemic brain injury such as a stroke or a secondary ischemic injury after a brain trauma, with stroke as an example.

Stroke is a severe, often-catastrophic disease affecting approximately 500,000 people per year in the U.S. Present methods of treatment except thrombolysis rely on supportive measures and non-specific agents. Twenty-five to sixty percent of stroke victims experience mild to severe disability, greatly increasing the long-term health related costs with aiding these patients. Therefore, there exists a need for improved methods of treating the morbidity experienced by these patients.

While intravenous thrombolytic treatments have shown promise, they generally require intervention within three hours of a stroke. Other unproven oral drug treatments may be initiated within a 24-hour post-stroke window and may positively affect neurological outcome with continued dosage for three months after a stroke.

One such method of protecting brain tissue from cerebral infarction subsequent to ischemia is disclosed in U.S. Pat. No. 5,827,832, issued to Sandage, Jr., et al. Sandage discloses an invention directed to a method of reducing the extent of infarction, and in particular, cerebral infarction subsequent to cerebral ischemia. Citicoline is administered shortly after an ischemic episode and continuing daily treatment for up to about 30 days, and in one preferred embodiment for at least about 6 weeks. The method taught is used for the treatment of stroke and severe head trauma patients and maximizes the chances for a full or substantially full recovery of the patient. The treatment regimen disclosed, however, uses citicoline, which is an exogenous form of cytidine-5'-diphosphocholine a key intermediate in the biosynthesis of membrane phosphatidyl choline, which is of primary importance for the dynamic regulation of cellular integrity. Furthermore the treatment protocol requires continued treatment for several weeks, with increased cost and likelihood of missing important doses.

Another method for treating central nervous system ischemia is disclosed in U.S. Pat. No. No. 5,571,840, issued to Mayor, et al., in which a patient who has suffered an acute insult is treated by administering an effective amount of a thyroid hormone. The thyroid hormones for use with the invention, as disclosed, include levothyroxine, liothyronine, L-3,3',5'-triiodothyronine or L-3,5-diiodothyronine, or their sodium salts. The treatment as taught is applicable to the treatment of cerebral ischemia following cardiac arrest. The thyroid hormones, however, have known short and long-term side effects and must be used with great care under a physicians close supervision.

SUMMARY OF THE INVENTION

The present invention improves upon this composition to better treat persons with ischemic brain injury as characterized by cerebral ischemia or ischemia associated with, and secondary to, brain injury.

In order to better treat persons with stroke and reduce the associated long-term and high cost of care, there is a need for improved treatment that may be both neuroprotive and able to reduce secondary brain injury associated with stroke. The present invention includes a method and composition adapted for the treatment of stroke. Applications in humans that may benefit from the use of the present invention include post-trauma surgery and other cardiac surgery (e.g., CABG, cardiopulmonary bypass), and persons with spinal cord injury, cerebral or cardiac emboli, cardiac arrest, stroke, subarachnoid hemorrhage, neurodegenerative diseases and combinations, thereof.

Generally, the present invention is a method adapted for the treatment of ischemic brain injury that includes applying hypothermic conditions to a subject after onset of brain injury and administering to the subject in need thereof a dose of a pharmaceutically effective amount of caffeine and a dose of a pharmaceutically effective amount of an alcohol (i.e. an alkanol) or mixtures thereof.

In another form, the present invention is a method adapted for the treatment of ischemic brain injury including the steps of applying hypothermic conditions to a subject within 5 hours after onset of brain injury, wherein said hypothermic condition includes reducing the body core temperature to at about 33–35 degrees Centigrade, and co-administering to the subject in nee d thereof a dose of a pharmaceutically effective amount of caffeine and a dose of a pharmaceutically effective amount of ethanol adapted for the treatment of cerebral ischemia under hypothermic conditions.

BRIEF DESCRIPTION OF THE DRAWINGS

For a more complete understanding of the features and further advantages of the present invention, reference is now made to the detailed description of the invention along with the accompanying FIGURES in which corresponding numerals in the different FIGURES refer to corresponding parts and in which.

DETAILED DESCRIPTION OF THE INVENTION

Figure 1:
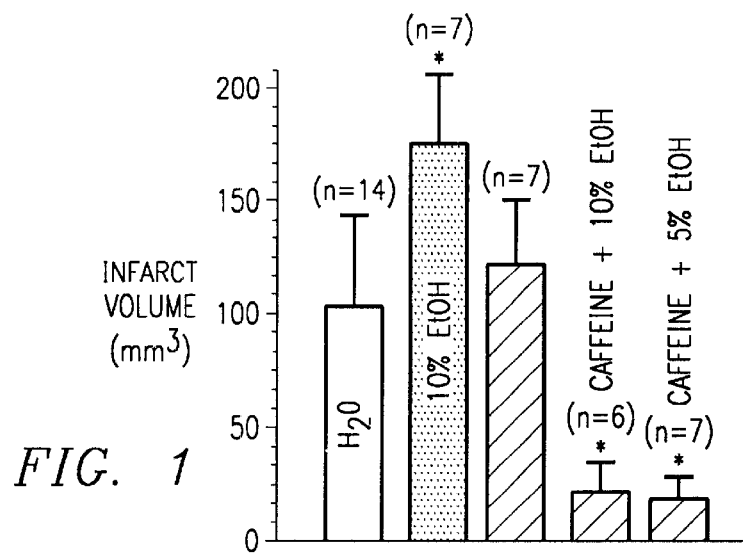
FIG. 1 depicts a graph showing the results obtained treating a type of ischemic cerebral damage orally using a method according to the present invention.

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a," "an," and "the" are not intended to refer to only a singular entity, but include the general class of which a specific example is used for illustration. The terminology herein is used to describe specific embodiments of the invention, but their usage does not limit the invention, except as outlined in the claims.

All technical and scientific terms used herein have the same meaning as commonly understood by one of ordinary skill in the art to which this invention belongs, unless defined otherwise The method of the present invention is adapted for the treatment of ischemic brain injury, such as a stroke or those injuries associated with, and secondary to, traumatic brain damage, in which "adapted for" means that the compounds are specifically selected and prepared for the method of the present invention and includes, without limitations, e.g., a compositions and method for the treatment of ill patients who must meet stringent requirements to be included as patients with ischemic brain injury. In addition, pharmaceutically effective doses of the mixture are discussed; "pharmaceutically active" is construed in the context of the treatment of ischemic cerebral damage.

Traumatic brain injury is a major health problem in all developed countries. Recent evidence has demonstrated clearly that traumatic brain lesions are highly dynamic and that the different lesions observed after closed head injury are not single events but processes set in motion by the mechanical impact. These processes are not finished until an as yet unpredictable time after injury. More importantly, primary immediate damage (such as diffuse axonal injury) can coexist with secondary damage (such as with axons that, although initially intact, may be evolving towards secondary disconnection).

In secondary damage, cerebral ischemia arises whenever delivery of oxygen and substrates to the brain falls below metabolic needs. Secondary brain insults arise through systemic or intracranial mechanisms that reduce cerebral blood flow from compromised coronary perfusion pressure (CPP), vascular distortion or cerebrovascular narrowing or lower oxygen delivery from hypoxemia associated with airway obstruction, pulmonary pathology, or anemia.

The role of excitotoxins in the ischemic cascade that results in ischemic neuronal death has been clearly defined and has brought about attempts to halt the progression of neurologic damage. Improved understanding of this process has allowed for the development of some interventions that help improve neurologic outcome following periods of ischemia.

The present inventors have recognized that deep hypothermia (15–22 degrees Centigrade) is one method of achieving neuroprotection, but is not without serious implications and risks to the patient. Mild hypothermia (32–35 degrees Centigrade) is evolving as an alternative neuroprotective measure that has been shown to improve neurologic outcome in experimental models of ischemia and head injury, as well as in recent head injury clinical trials. More recent work shows that prolonged post-ischemic hypothermia reduces neural damage and inhibits associated behavioral damage.

The present invention takes advantage of the benefits of hypothermia and is combined with doses of both caffeine and ethanol that are pharmaceutically effective for the treatment of stroke and that have a neuroprotective effect on persons with stroke. The present inventors have shown that pharmaceutical doses of caffeine and ethanol have proven beneficial as a method and composition adapted for the treatment of cerebral ischemic trauma Because caffeine and ethanol are frequently seen as a risk factor in cerebrovascular diseases, the resulting neuroprotective effect of caffeine and ethanol and the improved effects when combined with hypothermia were unexpected. No obvious mechanism of action of the combination could have been predicted.

The cerebroprotective action of the method disclosed herein was demonstrated in a rat model of transient focal cerebral ischemia in which the left middle cerebral artery (MCA) and left common carotid artery (CCA) was occluded with a stainless steel wire.

EXAMPLE 1

NEUROPROTECTIVE EFFECTS OF ETHANOL AND CAFFEINE

To demonstrate the neuroprotective effect of ethanol and caffeine, Long Evans rats, weighing between 300 and 350 grams, were randomly divided into five acute treatment groups. Group 1 had fourteen animals that were orally treated with deionized water. Group 2 had seven rats orally treated with caffeine alone. Group 3 included seven rats orally treated with ethanol alone. Groups 4 and 5 were groups treated with caffeine plus ethanol, one with 10% ethanol and the second with 5% ethanol in a carrier. In the present example the carrier was water, however other pharmaceutically acceptable carriers, water-based or not, may be used with the present invention.

The animals used in these studies were handled generally as follows: briefly, the rats were anesthetized with 400 mg/kg chloral hydrate administered intraperitoneally. The left femoral artery was cannulated with PE-50 polyethylene tubing for continuous monitoring of arterial blood pressure and blood sampling for analysis of arterial blood gases, femoral vein for intravenous infusion. A small burr hole in the cranium over the ischemic cortex was produced for continuous blood flow (CBF) monitoring. Rectal temperature was maintained at 37 degrees Centigrade with a thermostatically-controlled heating lamp during the surgery and MCA occlusion.

The right MCA was accessed through a 1×2 mm burr hole made right over the MCA with a metal wire (0.005" diameter) placed below the artery. The CCA was occluded with an aneurysm clip right after the MCA was occluded.

The MCA/CCA occluders and femoral artery and vein catheter were removed after a total ischemic period of 180 minutes, permitting reperfusion of the tissue. The animals were allowed to recover from the anesthesia and to eat and drink freely.

Rats randomly received treatment either orally 3 hours and 1 hour before or by intravenous (IV infusion) for 2.5 hours beginning 30, 60, 90, 120, or 180 minutes after ischemia. Group 1 was administered deionized water (dH$_2$O) orally, which served as the control group for this study. Group 2 was administered caffeine orally (2×10 grams/kg). In Group 3, a solution of 10% ethanol was provided orally (2×0.65 grams/kg total). Group 4 was orally administered 10% ethanol plus caffeine (10% ethanol at 0.65 grams/kg and 10 mg/kg caffeine), while Group 5 was given an intravenous solution of 10% ethanol (2×0.65 mg/kg) plus caffeine (2×10 mg/kg). In addition, a sixth group received, orally, 10% ethanol plus 10 mg/kg caffeine for 3 weeks prior to ischemia. After 3 hours of left MCA/CCA occlusion and 24 hours of reperfusion, infarct volume was determined using 2,3,5-triphenyltetrazolium chloride. The results are described herein below in association with the FIGURES.

Control deionized ($dH_2O$)-treated animals developed infarct volume that was 102.4+/−30.2 $mm^3$. Oral treatment with caffeine alone had no effect (122.4+/−30.2 $mm^3$). Oral ethanol alone, on the other hand, was found to exacerbate infarct volume (177.2+/−27.8 $mm^3$). Interestingly, oral caffeine plus ethanol almost entirely eliminated the damage (17.89+/−10.41 $mm^3$). When intravenous treatment with ethanol plus caffeine was initiated at 30, 60, 90 and 120 minutes post-ischemia the infarct volume was reduced to 33.07+/−17.49 $mm^3$ (n=6), 58.73+/−28.28 mm3 (n=6); 41.22+/−36.99 $mm^3$ (n=6) and 61.9+/−55.5 (n=9), respectively. The protective effect of intravenous ethanol plus caffeine was lost when treatment was delayed to 180 minutes post-ischemia 87.3+/−42.6 (n=8). Furthermore, chronic daily oral treatment with alcohol plus caffeine prior to ischemia eliminated the neuroprotection seen with acute treatment.

The combination of caffeine (10 mg/kg) plus ethanol (0.65 or 0.325 grams/kg) administered to rats subject to 180 minutes of unilateral middle cerebral/common carotid artery occlusion results in a dramatic reduction of the brain damage (infarct volume).

In contrast to the combination disclosed herein, caffeine alone did not modify infarct volume while ethanol produced significant augmentation of the damage. The combination of caffeine plus ethanol was effective in ischemia prophylaxis (oral 3 and 1 hour pretreatment reduced ischemic volume) and acute treatment (intravenous infusion of the combination initiated for up to 120 minutes post ischemia reduced ischemic damage).

FIG. 1 shows a summary of the results obtained using the present invention in the rat model system. The present inventors have discovered that an effective caffeine plus an alcohol mixture may include, for example, ethanol at either 5 (0.325 grams/kg) or 10 (0.65 grams/kg) percent, and that this mixture was able to dramatically reduce brain damage following an experimentally induced stroke as measured by infarct volume. Like results were not observed after treatment with deionized water as a control, or with treatment of caffeine or ethanol alone.

Figure 2:
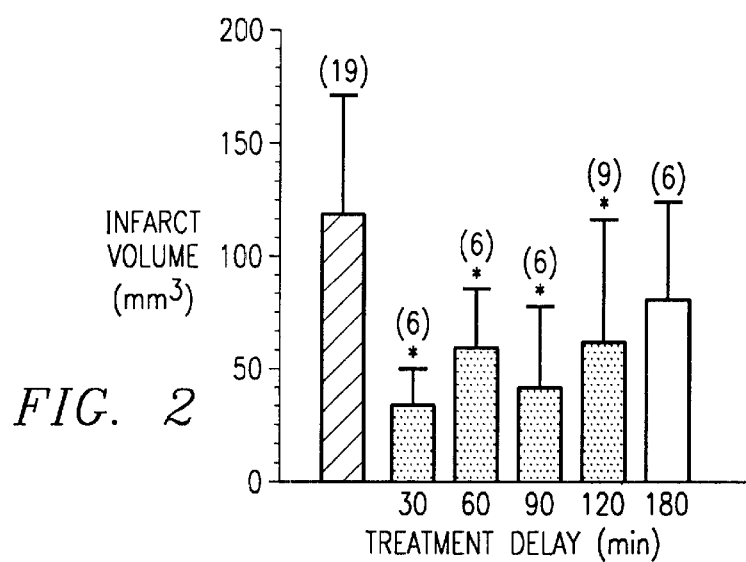
FIG. 2 depicts a graph showing the results obtained with intravenous treatment initiated at different time-points in accordance with the present invention.

FIG. 2 shows the results obtained using the above-referenced mixture in the rat model system in which the intravenous infusion of the mixture was delayed. The number above each of the bars is the number of rats used in each group in the study. As can be seen, the thirty- to ninety-minute delay treatment period appears to help protect the animal following an occlusive event, with the 90- and 120-minute delay in treatment offering a slightly lower level of protection.

Figure 3:
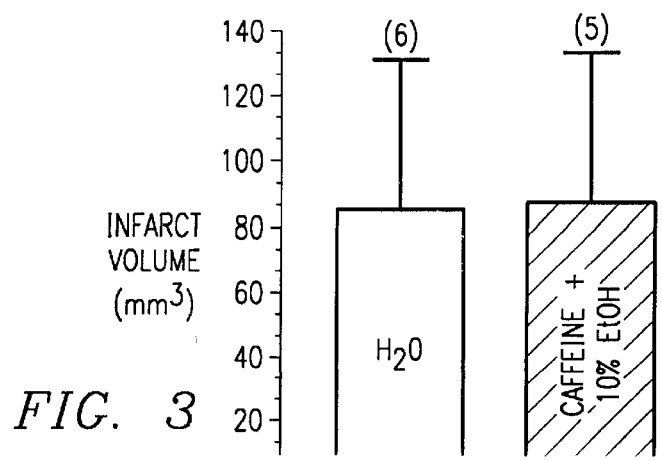
FIG. 3 depicts a graph showing that chronic oral pretreatment with a composition adapted for the treatment of ischemic cerebral damage prevents the protective effect observed with the acute treatment; in accordance with the present invention.

FIG. 3 shows the results obtained from the treatment of chronically treated rats prior to the ischemic event. Given chronic daily oral treatment with alcohol plus caffeine prior to ischemia eliminated the neuroprotection seen with 120- and 60- minutes pretreatment.

EXAMPLE 2

ETHANOL, CAFFEINE AND HYPOTHERMIA IMPROVE THE NEUROPROTECTIVE EFFECT OF ETHANOL AND CAFFEINE

The effect of ethanol plus caffeine can be further augmented by treatment in combination with mild (35° C.) hypothermia.

Study Groups for Hypothermia Plus Caffeine and Ethanol. In these studies four groups of animals were exposed to 180 minutes of reversible ischemia and 3 days of reperfusion. All anti-ischemic interventions were delayed for 60 minutes after the initiation of MCA/CCA occlusion (as discussed above), which is the earliest time at which treatment is likely to be given in humans, especially those who have just experienced a stroke or cerebral ischemic event resulting from traumatic brain injury.

The following four groups were evaluated: 1) ethanol plus caffeine (C/E); 2) 35° C. hypothermia (HYPOTH); 3) combined C/E+HYPOTH, and; 4) normothermic saline-treated control administered as in the C/E group.

The 35 degree Centigrade body core hypothermia was induced by placing the anesthetized rat on crashed ice. Hypothermia was started 60 minutes post-MCA/CCA occlusion and was sustained for 4 hours (with 2 hours of ischemia and 2 hours of reperfusion), followed by spontaneous re-warming. Intravenous caffeine and ethanol treatment were started 1 hour after onset of 180 minutes of ischemia and continued for 2.5 hours (see acute treatment discussed above).

Method of Infarct Volume Analysis. Morphometric determination of infarct volume was obtained with the help of computer based image analyzer operated by "Brain" software (Drexel University) as has been previously described. Infarcts produced by the above protocol are restricted to cortical tissue. The infarct volume ($mm^3$) was calculated from the difference between the volume of contralateral cortex and the volume of the TTC-stained (non-ischemic) portion of ipsilateral cortex of each rat. This indirect measure of infarct volume, based on the assumption that the volume of the ipsi- and contralateral cortex are the same prior to ischemia, corrects the total infarct volume for the edema component.

Figure 4:
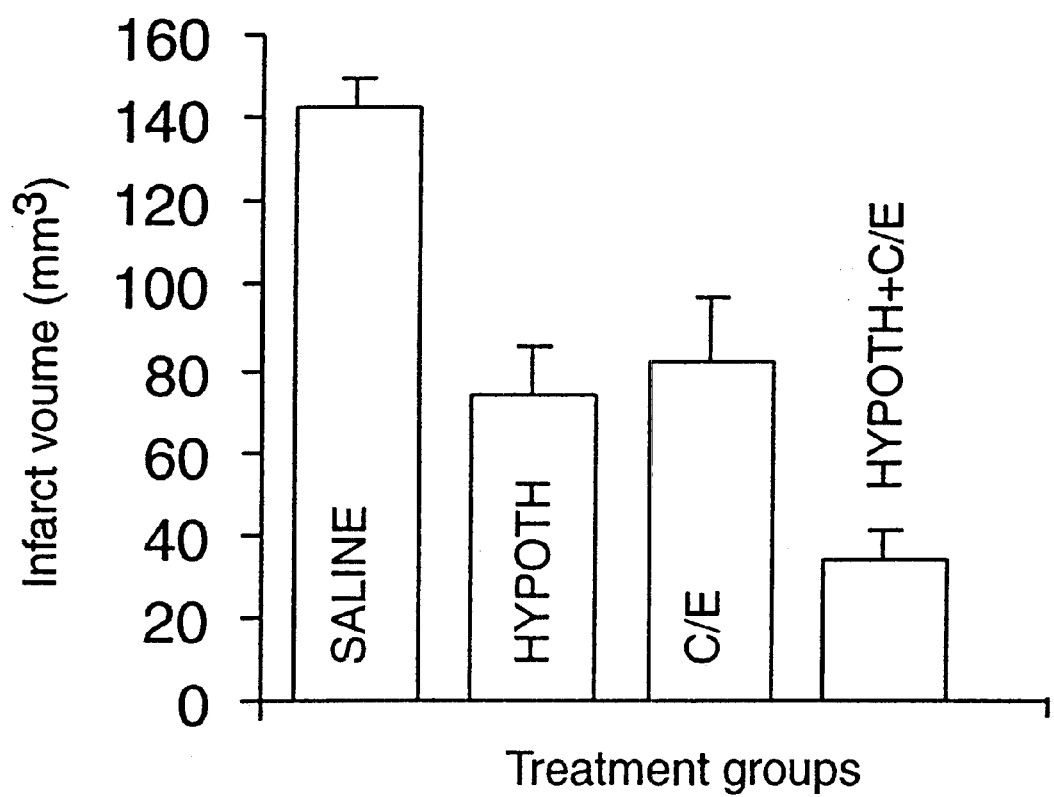
FIG. 4 depicts the comparison of infarct volume in four treatment groups exposed to reversible ischemia and three days of reperfusion with hypothermic conditions at the times indicated, in accordance with the present invention.

Results of all four groups are shown in FIG. 4. The results illustrate that for HYPOTH− (73.8+/−11.5 mm3; n=15), C/E− (81.7+/−15.2 mm3; n=16) and C/E+HYPOTH− (33.4+/−7.3 $mm^3$; n=18) treated groups, the infarct volume was different from the saline control (142.1+/−7.52 mm3; n=36)(p<0.05). Importantly, there was statistically significant improvement in the amount of protection of the ischemic brain with C/E+HYPOTH, as compared to all remaining groups (p<0.05); the effect of C/E+HYPOTH was significantly more than that of ether C/E or HYPOTH alone.

The therapeutic efficacy expressed by 0.32 g/kg ethanol plus 10 mg/kg caffeine as treatment for brain injury such as ischemia is further improved by the application of hypothermia, even when the application of hypothermia is greater than 1 hour after the onset of an injury associated with ischemia. This improvement in patient outcome may be further optimized for different types of brain injury or other events resulting in secondary brain injury associated with ischemia. For example, hypothermia may be applied within less than 2 hours after injury or later than 3 hours after injury, depending on type and severity of the injury as well as other mitigating circumstances, as is apparent to those of skill in the art. Those skilled in the art will be able to optimize patient outcome and improve treatment results without undue experimentation.

While the present invention has been described in reference to illustrative embodiments, the above description is not intended to be construed in a limiting sense, additional alternatives not specifically disclosed but known in the art are intended to fall within the scope of the invention. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method for treating brain injury comprising the steps of:
    applying hypothermic conditions to a subject after onset of brain injury; and
    administering to the subject a composition comprising effective amount of caffeine and an effective amount of an alkanol.
2. The method of claim 1, wherein said alkanol is ethanol.
3. The method of claim 1, wherein said composition is administered no later than about 24 hours after the occurrence of a traumatic brain injury.
4. The method of claim 1, wherein said effective amount of caffeine ranges from about 100 mg to about 5000 mg.
5. The method of claim 1, wherein said caffeine and said alkanol are co-administered.
6. The method of claim 1, wherein the caffeine is in the form of a pharmaceutically acceptable salt.
7. The method of claim 1, wherein said administration of said composition is carried out over a period of at least about 3 days.
8. The method of claim 1, wherein said composition is administered one or more times daily over a predetermined period.
9. The method of claim 1, wherein said hypothermic conditions comprise reducing the body core temperature to at least about 35 degrees Centigrade and maintaining this temperature for at least about 3 hours.
10. The method of claim 1, wherein said hypothermic conditions are applied about 1 hour after onset of said brain injury.
11. The method of claim 1, wherein the subject is human.
12. The method of claim 1, wherein the subject is a rat, further defined as a rat model for stroke.
13. The method of claim 1, wherein said composition is administered at about the time of applying said hypothermic conditions.
14. The method of claim 1, wherein said composition further comprises a therapeutic agent selected from the group consisting of t-PA, streptokinase, urokinase, aspirin, dipyridamole, and combinations thereof.
15. A method for treating a subject with cerebral ischemia comprising the steps of:
    applying hypothermic conditions to the subject as soon after the onset of ischemic brain injury as possible, wherein said hypothermic conditions include reducing the body core temperature to at least about 35 degrees Centigrade; and
    administering to the subject a composition comprising an effective amount of caffeine and an effective amount of ethanol.
16. The method of claim 15, wherein said composition is administered no later than about 24 hours after the occurrence of said ischemic brain injury.
17. The method of claim 15, wherein said pharmaceutically effective amount of caffeine ranges from about 100 mg to about 5000 mg.
18. The method of claim 15, wherein said composition is administered within about 12 to about 15 hours after the occurrence of ischemic brain injury which is caused by a traumatic brain injury.
19. The method of claim 15, wherein the caffeine is in the form of a pharmaceutically acceptable salt.
20. The method of claim 15, wherein said hypothermic conditions are maintained for at least about 3 hours.
21. The method of claim 15, wherein said composition is administered at about the time of applying said hypothermic conditions.

* * * * *